US007125911B2

(12) United States Patent
Nagashima et al.

(10) Patent No.: US 7,125,911 B2
(45) Date of Patent: Oct. 24, 2006

(54) AUTONOMIC NERVE REGULATING AGENT

(75) Inventors: Yoshinao Nagashima, Tokyo (JP); Keiichi Sugata, Tokyo (JP); Yukihiro Yada, Tokyo (JP); Kazuyuki Fukuda, Tokyo (JP)

(73) Assignee: Kao Corporation, Tokyo (JP)

( * ) Notice: Subject to any disclaimer, the term of this patent is extended or adjusted under 35 U.S.C. 154(b) by 211 days.

(21) Appl. No.: 09/972,887

(22) Filed: Oct. 10, 2001

(65) Prior Publication Data

US 2002/0151600 A1 Oct. 17, 2002

Related U.S. Application Data

(63) Continuation of application No. PCT/JP01/00928, filed on Feb. 9, 2001.

(30) Foreign Application Priority Data

Feb. 10, 2000 (JP) .............................. 2000-038260

(51) Int. Cl.
A61K 31/045 (2006.01)
A61K 31/05 (2006.01)
(52) U.S. Cl. ..................... 514/729; 514/733; 514/739
(58) Field of Classification Search ................ 514/729, 514/733, 739
See application file for complete search history.

(56) References Cited

U.S. PATENT DOCUMENTS

| 3,632,782 A | * | 1/1972 | Alburn et al. ............... 514/731 |
| 4,713,291 A | * | 12/1987 | Sasaki et al. ................ 428/373 |
| 5,095,015 A | * | 3/1992 | Albaugh ................ 514/212.06 |
| 5,195,514 A | * | 3/1993 | Liu et al. ............... 128/203.17 |

FOREIGN PATENT DOCUMENTS

| EP | 0 183 436 A2 | | 11/1985 |
| EP | 1031348 | * | 8/2000 |
| FR | 2697133 | * | 4/1994 |
| FR | 4 055 M | | 5/1996 |
| GB | 294 587 | | 7/1928 |
| JP | 61-33129 | | 2/1986 |
| JP | 61-267526 | | 11/1986 |
| JP | H4-128234 | | 4/1992 |
| JP | 04-210602 | | 7/1992 |
| JP | H5-255688 | | 10/1993 |
| JP | H6-40911 | | 2/1994 |
| JP | 08-225437 | | 9/1996 |
| JP | 09-020646 | | 1/1997 |
| JP | H10-25245 | | 1/1998 |
| JP | 10-036246 | | 2/1998 |
| JP | H10-113369 | | 5/1998 |
| JP | H11-343497 | | 12/1999 |
| JP | 2000-42125 | | 2/2000 |
| JP | 2001-049286 | | 2/2001 |
| WO | WO 97/32611 | | 9/1997 |
| WO | WO 1/58435 A1 | | 8/2001 |

OTHER PUBLICATIONS

Sawada et al, 132CA:332157, 1999.*
Binet et al. 78CA:24110, 1972.*
Binet et al. "Farnesol, a psychosedative and spasmolytic compound" 1972, Therapie, 27(5), 893-905.*
Buchbauer et al. "Fragrance Compounds and Essential Oils with Sedative Effects Upon Inhalation" 1993, Journal of Pharmaceutical Science, 82(6), 660-4.*
Toshimitsu Musha, Ph.D., Shin Kimura, M.S., Ken-ichi Kaneko, Kiyoko Nishida, and Kazuo Dekine, Emotion Spectrum Analysis Method (ESAM) for Monitoring the Effects of Art Therpay Applied on Demented Patients, CybrPsychology & Behavior, vol. 3, No. 3, 2000, pp. 441-446, Mary Ann Liebert, Inc.
Abstract, Patent No. JP 10025245, Application No. JP 96182349, Jan. 27, 1998, "Oral Hypnotic Agent Used for Medicines, Foods; Drinks and Feeds Contain Essential Oil of Sandalwood".
Abstract, Patent No. JP 11343497, Application No. JP 98188008, Dec. 14, 1999, "Cosmetics Showing Sedative and Hypnotic Effect Comprising Flavour of Rosemary, Lavendar, Bitter Orange or Senkyu".
Abstract, Patent No. JP 4128234, Application No. JP 90249716, Apr. 28, 1992, "New Sleep Promoting Agent Comprises Bitter Orange Essential Oil, Formulated for Absorption Through the Nasal Mucosa or the Lungs".
Abstract, Patent No. JP 6040911, Feb. 16, 1994; Application No. JP 92195333, Jul. 22, 1992; "Sleep Promoter Containing Jasmine Lactone as Active Component is in the Form of Preparation Where Active Component is Absorbed from Lung or Nose or Mouth Mucosa".
Abstract, Patent No. JP 5255688, Oct. 5, 1993; Application No. JP 9289811, Mar. 13, 1992; "Perfume Containing Sedative Essential Oil has Durable Sedative Effect".
Abstract, Patent No. JP 10113369, May 6, 1998; Application No. 9770225, Mar. 24, 1997; (WO 9807403); "Cosmetological Method for Achieving Valuable Cosmetic Effects Easily by Massage Comprising Massage Carried out by Ordinary People Along Arterial and then Venous Blood Flow Paths Using Cosmetic Containing Disintegrative Particles".
Derwent Publications, AN 1994-239062, XP-002293818, JP 06 172781, Jun. 21, 1994.
A. L. Leung, et al., Encyclopedia of Common Natural Ingredients Used in Food, Drugs, and Cosmetics, XP-002152519, pp. 139-141 and 411-413, "Cedarwood Oil", 1996.
Japanese May 16, 2006 Notification of Research for Refusal (JP Patent Appln. No. 2001-557546).
The Fragrance Journal, 1992, Vo. 20, No. 8, pp. 106-111 -Japanese Language w English language Abstract-See paragraph on p. 106).

* cited by examiner

*Primary Examiner*—Sreeni Padmanabhan
*Assistant Examiner*—Jennifer Kim
(74) *Attorney, Agent, or Firm*—Oblon, Spivak, McClelland, Maier & Neustadt, P.C.

(57) ABSTRACT

The autonomic nerve regulating agent of the present invention, which, has sedative action, sleep inducing action, and stress mitigating action in individuals, regardless of individual variation in sensitivity to or preference for fragrance, contains as an active ingredient a sesquiterpene alcohol with a boiling point of 250° C. or higher, particularly cedrol.

24 Claims, 18 Drawing Sheets

Before inhalation of Cedrol (in rest)

After inhalation of Cedrol

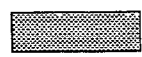 Before inhalation of Cedrol (in rest)
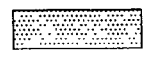 After inhalation of Cedrol Continuous fluctuation in sleep stages 3 and 4

▓ Before massaging
░ 4 weeks after the beginning of massaging

*:p<0.05   **:p<0.01

*:p<0.05   **:p<0.01

*: $p<0.05$  **: $p<0.01$

**:p<0.01
*:p<0.05

**: p<0.01
*: p<0.05

**:p<0.01

**:p<0.01

**:p<0.01

**:p<0.01

**:p<0.01

<Vapor Pressure of Cedrol vs. Temperature>

| Temp.(°C) | Vapor Pressure (mmHg) | Vapor density (ideal gas) | Measuring method |
|---|---|---|---|
| 22 | 1.50E-04 | 1.81ppb | Gas flow method |
| 50 | 5.10E-03 | 56.2ppb | Gas flow method |
| 75 | 7.60E-02 | 0.777ppm | Gas flow method |
| 100 | 7.00E-01 | 6.68ppm | Static method |
| 125 | 4.05 | 36.2ppm | Static method | ated by odor perceptions, but also provides an autonomic
AUTONOMIC NERVE REGULATING AGENT

BACKGROUND OF THE INVENTION

1. Field of the Invention

The present invention relates to an autonomic nerve regulating agent having sedative action, sleep improving action, stress mitigation action, and the like.

2. Discussion of the Related Art

When the balance between the activities of the parasympathetic nervous system and the sympathetic nervous system is upset by physical and mental stress, the resulting disequilibrium in the autonomic nervous system can lead to mental aggravation, making it difficult to fall asleep very easily (sleep induction) and resulting in shallow sleep. It is believed that stimulating the physiological predominance of the parasympathetic activity over the sympathetic activity can reduce stress and calm aggravated mental states, thus inducing favorable sleep.

Methods that have long been used to thus stimulate the predominance of the parasympathetic activity over the sympathetic activity include the oral or percutaneous administration of active ingredients to humans, as well as aromatherapy involving vaporizable fragrance compositions to allow the vapors to be inhaled. Recent proposals include methods in which bitter orange essential oil (Japanese Laid-Open Patent Application Kokai) H4-128234) and jasmine lactone (Japanese Laid-Open Patent Application (Kokai) H6-40911) are administered by absorption via the nasal mucosa, oral mucosa, or pulmonary tissue for better sleep induction.

The use of the low-boiling components of cedar wood oil (such as α-pinene, α-cedrene, β-cedrene, and caryophyllene) as a sedative essential oil has also been proposed (Japanese Laid-Open Patent Application (Kokai) H5-255688).

It is not altogether clear-whether or not the effects of such fragrances or essential oil components are determined solely by their action on the autonomic nervous system, and it has been assumed that action mediated by other physiological routes, including the lower central nervous system, may be involved.

There is substantial individual variation in the sensitivity to and preference for scents (fragrances) such as bitter orange essential oil and jasmine lactone. While these may have sedative and sleep inducing action for some people, they may on the contrary be disagreeable or irritating to others. There is thus a need for a component or method capable of universally improving autonomic nervous imbalances (in other words, restoring the balance to a physiologically ideal state) whose effects are not biased by odor perceptions.

The low-boiling components of cedar wood oil have a strongly characteristic fragrance, and their sedative actions are also subject to considerable individual variation in terms of people's sensitivity and preferences in the same manner as bitter orange essential oil and the like.

SUMMARY OF THE INVENTION

An object of the present invention is to provide an autonomic nerve regulating agent, sleep improving agent, and agent for mitigating stress (henceforth referred to as autonomic nerve regulating agents) which have a sedative action and the like for individuals whose sympathetic activity is predominant, irrespective of the variation in individual sensitivity or preference for fragrances, and conversely have action in restoring the physiological balance to within normal range in individuals whose parasympathetic activity is predominant.

The inventors have discovered that emotions (moods) can be effected or modified by some compounds which belong to sesquiterpene alcohols. These compounds are substantially odorless, that is, having an odor below the detectable threshold (in other words, causing no notice of preference). Nevertheless, they have sedative or sleep improving action on individuals whose sympathetic activity is predominant (said action stimulating the predominance of the parasympathetic activity over the sympathetic activity). Also they conversely have action in stimulating the predominance of the sympathetic activity over the parasympathetic activity to restore the physiological balance to within normal range in individuals whose parasympathetic activity is predominant, and have an odor substantially below the detectable threshold.

That is, the present invention provides an autonomic nerve regulating agent, a sleep improving agent, or a stress mitigating agent, comprising sesquiterpene alcohol with a boiling point of 250° C. or higher with essentially no detectable odor. By having an odor substantially below the detectable threshold, the autonomic nerve regulating agents described herein can be administered to people without resulting in negative or adverse reactions to the odors and fragrances commonly associated with aromatherapy.

Another object of the present invention is to provide a vaporization system comprising a vaporization-promoting element and a composition comprising a sesquiterpene alcohol having an odor substantially below the detectable threshold and with a boiling point of 250° C. or higher.

The present invention also affords an autonomic nerve regulating method, a sleep improving method, and a stress mitigation method.

DESCRIPTION OF THE PREFERRED EMBODIMENTS

Figure 1:
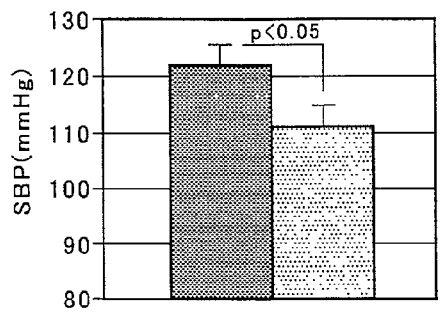
FIGS. 1A through 1F illustrate the measurement results for the various test parameters of the autonomic nerve regulating agent in Example 1.
Figure 1:
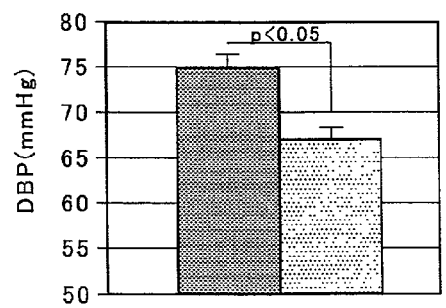
Figure 1:
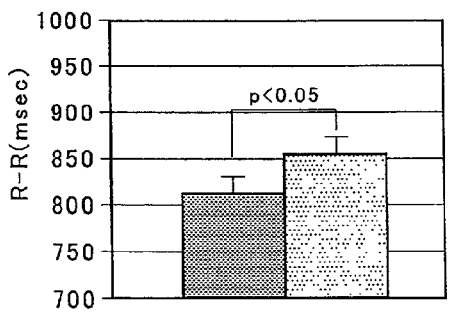
Figure 1:
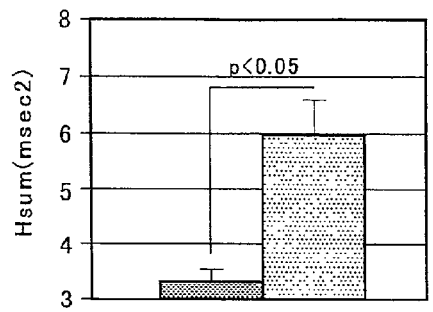
Figure 1:
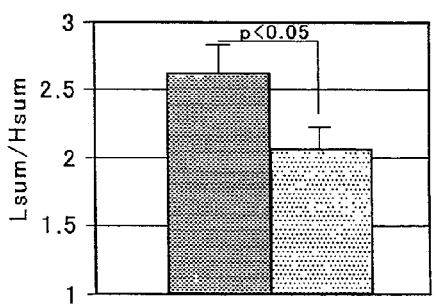
Figure 1:
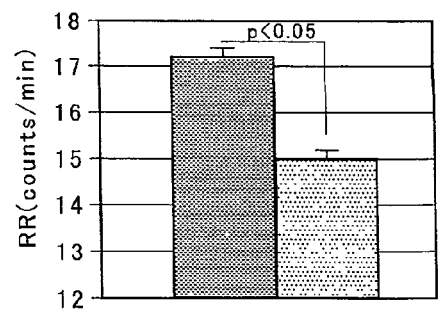

The autonomic nerve regulating agents of the present invention comprise a sesquiterpene alcohol with a boiling point of 250° C. or higher at atmospheric pressure, as compounds which have sedative action and sleep improving action for individuals whose sympathetic activity is predominant, and which conversely have action in stimulating the sympathetic activity to predominance over the parasympathetic activity in individuals whose parasympathetic activity is predominant, as well as in improving emotions such as anger, stress, sense of joy or sadness, and relaxation (specifically, relieving stress and anger, enhancing a sense of joy, mitigating sadness, and enhancing a sense of relaxation). At least part of the mechanism resulting in such action is attributed to reception via the primary olfactory nervous system and stimulation of the autonomic nervous system through the lower central nervous system, with the additional possibility that the higher central nervous system is stimulated via the lower central nervous system.

As used in the present invention, "autonomic nervous regulation" indicates improvement of disequilibrium in the autonomic nervous system within a nonmorbid range, defined as at least one, preferably at least two, and even more preferably at least three of the following phenomena (1) through (6), as determined in accordance with the following examples in subjects whose sympathetic activity is greater than usual:

(1) meaningful decrease of systolic blood pressure (SBP);
(2) meaningful decrease of diastolic blood pressure (DBP);
(3) meaningful extension of R—R interval in ECG;
(4) meaningful increase of Hsum in R—R interval fluctuations;
(5) meaningful decrease of Lsum/Hsum in R—R interval fluctuations; and
(6) meaningful reduction of respiratory rate.

Examples of sesquiterpene alcohols with a boiling point of 250° C. or higher having action capable of inducing such phenomena include cedrol (boiling point 295° C.), cedrenol (boiling point 270° C.), farnesol (boiling point 263° C.), patchouli alcohol (boiling point 140° C/8 mmHg), eugenol (boiling point 254–255 C), α-santalol (boiling point 302° C.), α-bisabolol (boiling point 265° C.), β-caryophyllene alcohol (boiling point 287–297° C.), vetiverol (bailing point 264° C.), sclareol (boiling point 340° C. or higher), geranyl linalool (boiling point 340° C.), isophytol (boiling point 310° C. or higher), and nerolidol (boiling point 276° C.), as well as globulol and guaiol. Of these, sesquiterpene alcohols having an odor substantially below the detectable threshold, are preferred, while cedrol is particularly preferred because it affords excellent effects in the invention and is readily available. Cedrol of low purity is considerably affected by other fragrance components and is hard to obtain in crystalline form with good handling properties. The purity is thus preferably at least 70%, more preferably at least 80%, even more preferably at least 90%, still more preferably at least 95%, and especially at least 97%.

"An odor substantially below the detectable threshold" means an odor that cannot be detected by at least 5, and preferably 8 or more, individuals among 10 Japanese individuals with normal olfactory function.

The volatile, low boiling components thought to be responsible for the odors and fragrances associated with, for example, cedar wood oil, jasmine lactone and bitter orange essential oil are not present in the autonomic nerve regulating agents described herein at concentrations ordinarily detectable by humans. Sesquiterpene alcohols that are free of low boiling components are essentially odorless. These autonomic nerve regulating agents may include sesquiterpene alcohols having a boiling point of greater than 150° C., preferably greater than 200° C., and most preferably greater than 250° C.

The amount of the sesquiterpene alcohol with a boiling point of 250° C. or higher (at atmospheric pressure) that is used in the present invention can be determined as desired according to the intended application of the autonomic nerve regulating agents (such as miscellaneous goods, including base cosmetics, make-up cosmetics, hair cosmetics, bathing agents, poultices, massaging agents, indoor fragrances, and masks; food products and beverages, including functional food products; tooth paste or mouth washes; various fiber products, including seat covers, bedding, wall paper, furniture, and clothing) or according to the formulation that is used (such as solutions, solids, powders, sprays, gels, and pastes). When used as a lotion, for example, the amount is preferably 0.01 to 0.05 wt % in consideration of the dissolution stability of the sesquiterpene alcohol. When used as an emulsion or cream, the amount is preferably 0.01 to 7.50 wt % in the consideration of the emulsion stability. When used in the form of a bathing agent, the type of formulation and the amount may be selected so as to result in a concentration of at least 0.01 ppm, preferably 0.1 to 1000 ppm, and even more preferably 5 to 1000 ppm, in-the bath water.

Where in this application a range is provided all values and subranges between the stated ranges are expressly included. For example the range 0.01 to 7.50% includes all between lying values including, for example, 5, 2, 1, 0.5 and 0.05 etc. %.

Various additives commonly used in a variety of applications (such as oils, fillers, colorants, polymers, humectants, UV absorbents, pH adjusting agents, antioxidants, surfactants, and fragrances) can be blended as desired in the autonomic nerve regulating agents of the present invention according to the intended application and the formulation that is used.

The autonomic nerve regulating agents of the present invention can be administered to humans through respiration, the oral mucosa, the nasal mucosa, orally, transdermal penetration, or via the respiratory tract. Autonomic nerve regulating agents of the present invention, such as orally administered tablets, need not necessarily contain the sesquiterpene alcohol in a vaporizable state. However, for administration to a large, unspecified number of individuals, an extremely low concentration of sesquiterpene alcohol is preferably dispersed in the space and its vicinity where the administration takes place, so as to allow it to be administered through the nasal mucosa or respiratory tract through the natural respiration of the individuals. The autonomic nerve regulating agents of the present invention thus preferably contain a sesquiterpene alcohol such as cedrol in a vaporizable state. The vaporizable state means a state in which the material is dispersed in the form of vapor, minute solid particles, or droplets into the air, either through natural vaporization or as a result of treatment such as heating, ultrasonic irradiation, steam heating, or negative (or minus) ionization with a vaporization-promoting element.

The method of using the autonomic nerve regulating agents of the present invention can also be determined as-desired according to-the intended application and the formulation that is used. For example, when used in the form of a pad soaked with a sesquiterpene alcohol having a boiling point of 250° C. or higher, the pad may be heated by means of heat generated by a vaporization-promoting element such as an electric heater to allow the sesquiterpene alcohol to be vaporized, or it can be heated by hot steam produced by a vaporization-promoting element such as the mask described in Japanese Laid-Open Patent Application (Kokai) 2000-42125, which comprises a water vapor-producing element, to allow the sesquiterpene alcohol to be vaporized. When a sesquiterpene alcohol having a boiling point of 250° C. or higher is solubilized in aqueous media, liquid droplets containing the sesquiterpene alcohol can be vaporized through the application of ultrasonic waves from a vaporization-promoting element such as an ultrasonic humidifier, or the sesquiterpene alcohol can be vaporized through negative ionization by means of a device for breaking up water which involves exploiting the Lenard effect. In these cases, the sesquiterpene alcohol should be vaporized at a concentration of between 0.01 to 100 ppb in the air, as too low a concentration will not afford the desired results, while too high a concentration will result in the condensation of fine particles in the air.

The sesquiterpene alcohols in the present invention may also be vaporized naturally at ambient temperature without the aforementioned treatment. That is, embodiments using sesquiterpene alcohol in a vaporizable state are not limited to the use of a vaporization- promoting element, and can also include simply spraying the autonomic nerve regulating agent containing sesquiterpene alcohol on bedding or wall paper; so-called "leave on" types of cosmetics which are applied to the skin without being washed off; and compositions which are used by being left for a certain period of time in the mouth (such as tooth paste or candy)

As noted above, through their action on the autonomic nervous system, the sesquiterpene alcohols in the present invention are capable of mitigating physical or mental stress and of soothing aggravated mental states. Also they are capable of improving the quality of sleep, such as shortening the sleep latency (the time it takes an individual to fall asleep), reducing the number of intermittent awakening and shortening the time needed to wake up, improving sleep efficiency (=total sleep time/time in bed), enhancing the good feeling upon waking, and prolonging the period of deep sleep (non-REM sleep). The present invention is thus suitable for use as a sleep improving agent.

As used in the present invention, "sleep improvement" indicates the qualitative or quantitative improvement of sleep within the nonmorbid range, defined as at least one, preferably at least two, and more preferably three or more of the following (1) through (4), as determined in accordance with the following examples in subjects who suffer from poor sleep:

(1) meaningful shortening of sleep latency;
(2) meaningful reduction of number of intermittent awakening;
(3) meaningful increase of sleeping efficiency; and
(4) meaningful improvement in terms of tension and fatigue based on POMS.

The sesquiterpene alcohols of the present invention also have an effect on the expression of emotions (moods) and the state thereof, which is influenced by the higher central nervous system governing preferences. Specifically, they allow composure to be recovered, anger/stress or sadness to be controlled, and a sense of joy and relaxation to be enhanced. The present invention is thus suitable for use to relieve stress.

Such changes of emotion can be determined by emotion spectrum analysis based on brain waves (T. Mushy et al., "Emotion spectrum analysis method (ESAM) for monitoring the effects of art therapy applied on demented patients," *Cyber Psychology & Behavior,* 3, 441–446 (2000), the relevant portions thereof which describe emotion spectrum analysis are incorporated herein by reference).

As used in the present invention, "stress mitigation" indicates that mental or physical stress is mitigated within the nonmorbid range, defined as improvement in at least one, preferably at least two, and more preferably three or more of the parameters of "anger/stress," "joy," "sadness," and "relaxation" by emotion spectrum analysis as determined in accordance with the following examples for subjects experiencing stress.

By providing effects such as sleep improvement and stress mitigation, the present invention can also improve menopause, PMS (premenstrual syndrome), physical vitality and appetite.

The use of a compound with odor substantially below the detectable threshold, particularly cedrol, from among the sesquiterpene alcohols employed in the present invention allows the autonomic nerve regulating agents of the present invention to produce the aforementioned effects in individuals or an unspecified number of individuals, regardless of their disposition towards fragrances. The autonomic nerve regulating agents of the present invention can accordingly be used not only in private spaces such as bedrooms and bathrooms, but also in public spaces such as meeting rooms, private rooms, airplanes, vehicles, hotels, nursing facilities, hospitals, nursing homes, public health facilities, department stores, airports, libraries, stations, and business offices, in any configuration or at any period of time (such as morning, afternoon, evening, before bed, after bed, during work, or during exercise) or for any physical condition (such as during fatigue, good health, or stress).

A sesquiterpene alcohol with a boiling point of 250° C. or higher can be directly vaporized as needed by a vaporization system comprising the aforementioned vaporization-promoting element and a composition such as an autonomic nerve regulating agent, stress mitigating agent, and sleep improving agent comprising a sesquiterpene alcohol with a boiling point of 250° C. or higher in a vaporizable state as needed combined with a desired carrier or medium.

It is not necessary to operate the vaporization-promoting element throughout the entire sleeping period in order to achieve the sleep improving effects, for example. Satisfactory effects will be achieved with shorter periods of time, such as about 30 minutes to 2 hours of operation, before going to bed and a short time after falling asleep.

This application is based on and claims benefit of priority to International Application PCT/JP01/00928 filed on Feb. 9, 2001 and Japanese priority document JP 2000-38260 filed on Feb. 10, 2000, each of which is incorporated by reference in its entirety.

EXAMPLES

The present invention is illustrated in further detail in the following examples.

Reference Example 1

The vapor pressure of purified cedrol (molecular weight 222 g·mol$^{-1}$) used in the following examples was determined by a static method and a gas flow method (temperature: 22, 50, and 75° C. for solids; 100 and 125° C. for liquids).

In the static method, samples were taken from hermetically sealed containers, a constant temperature was established, and the equilibrium vapor pressure at that temperature was directly measured using a pressure gauge (OECD Test Guidelines 104: Static Measurement of Vapor Pressure).

In the gas flow method, carrier gas (nitrogen gas) was allowed to flow so as to come into contact with a solid or liquid sample at a certain temperature to saturate the sample vapor, and the vapor density (vaporization quantity/volume) was measured so as to determine the vapor pressure hypothetically in accordance with ideal gas principles. The vapor density herein referred to is calculated from the sample vaporization rate (rate of loss) determined using an electrical balance, and the carrier gas flow rate determined using a flow rate gauge. However, since the sample vapor saturation is usually incomplete, the vapor density level is dependent on flow rate, so the vapor density was measured at varying flow rates for extrapolation to a zero flow rate to determine the saturated vapor density. The following formula was used to determine the vapor pressure from the vapor density, $$P=(k/v)V\pi/M$$

(where P is the vapor pressure (mmHg), k is the vaporization rate (mg/min), v is the carrier gas flow rate (ml/min), k/v is the vapor density (mg/ml.), V is the carrier gas molar volume (L/mol), $\pi$ is the system pressure (mmHg), and M is the sample molecular weight; 1 mmHg=1.33×10$^2$Pa).

Figures 18, 19:
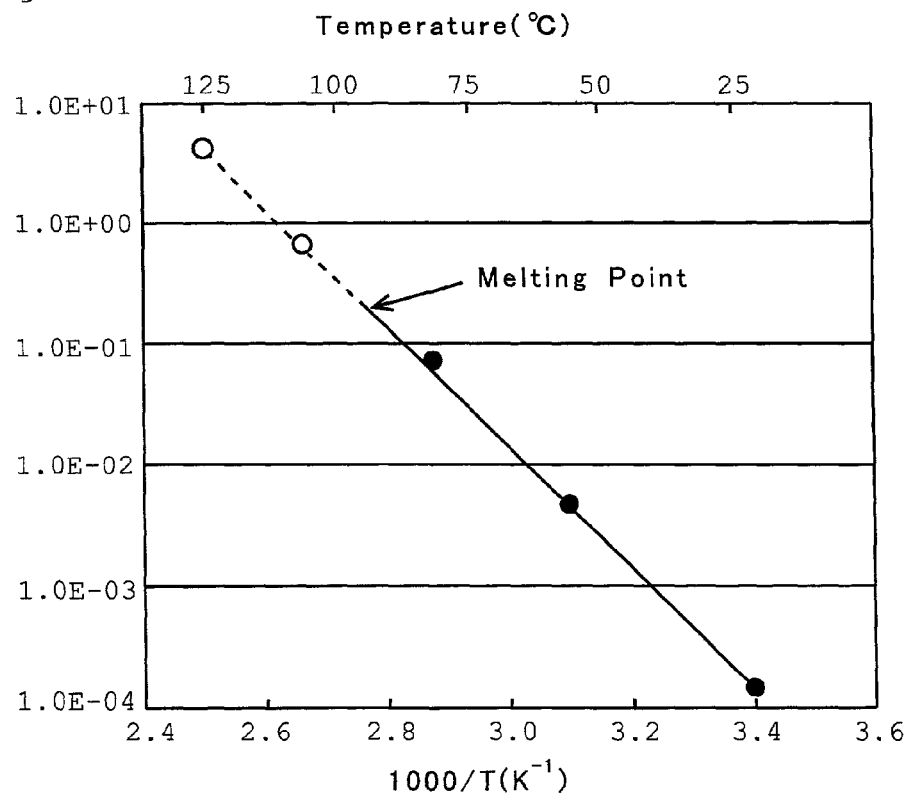
FIG. 18 is a table of the measurement results for vapor pressure of cedrol.
FIG. 19 is a curve of the vapor pressure of cedrol.

The results are given in FIG. 18, and are plotted on a graph (FIG. 19).

The results show that cedrol can be vaporized at ambient temperature (unheated).

Example 1

The subjects were ten women in their twenties complaining of fatigue (sympathetic overactivity), who were asked to inhale, for 30 seconds, cedrol dissolved in dipropylene glycol (10 wt % concentration), while ECG at rest (chest V5 lead), blood pressure (tonometry), and respiration (pulmonary volume instantaneously measured by respiratory rate sensor) were monitored. The changes in parameters before and after measurement were compared. Frequency analysis of R—R interval fluctuations was performed for low frequency components integrating amplitudes 0.02 to 0.12 Hz (sum of low frequency: Lsum) and high frequency components integrating amplitudes 0.12 to 2.00 Hz (sum of high frequency: Hsum) using the rapid Fourier transform. As used here, the Hsum is an indicator of parasympathetic nervous activity, and the Lsum/Hsum is an indicator of sympathetic nervous activity.

The measurement results were statistically analyzed by Welch's t-test or Student's t-test based on the F test.

Results

1) The systolic blood pressure (SBP) was meaningfully lower (5%) after inhalation compared to before inhalation (FIG. 1A).

2) The diastolic blood pressure (DBP) was meaningfully lower (5%) after inhalation compared to before inhalation (FIG. 1B).

3) The ECG R—R interval was meaningfully longer (5%) after inhalation compared to before inhalation (FIG. 1C).

4) The Hsum was meaningfully greater (5%) after inhalation compared to before inhalation (FIG. 1D).

5) The Lsum/Hsum was meaningfully lower (5%) after inhalation compared to before inhalation (FIG. 1E).

6) The respiratory gate (RR) was meaningfully lower (5%) after inhalation compared to before inhalation (FIG. 1F).

Conclusions

The above results demonstrate that the inhalation of cedrol by the subjects resulted in sedative effects in various parts of the body, suppressed sympathetic overactivity, and resulted in the predominance of the parasympathetic activity.

Example 2

The subjects were ten insomniac women in their twenties (under considerable pressure to get to sleep, with parasympathetic predominance to excess), who were asked to inhale, for 30 seconds, cedrol dissolved in dipropylene glycol (10 wt % concentration), while ECG at rest (chest V5 lead), blood pressure (tonometry), and respiration (pulmonary volume instantaneously measured by respiratory rate sensor), and skin blood flow of forehead (measured by laser Doppler methods) were monitored. The changes in parameters before and after measurement were compared. Frequency analysis of R—R interval fluctuations and statistical analysis of the measurement results were done in the same manner as in Example 1.

Results

Figure 2A:
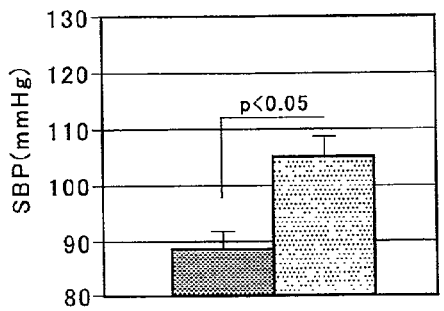
FIGS. 2A through 2F illustrate the measurement results for the various test parameters of the autonomic nerve regulating agent in Example 2.

1) The systolic blood pressure (SBP) was meaningfully higher (5%) (within physiologically normal range) after inhalation compared to before inhalation (FIG. 2A).

Figure 2D:
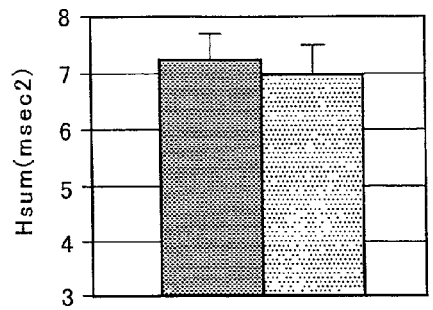
Figure 2B:
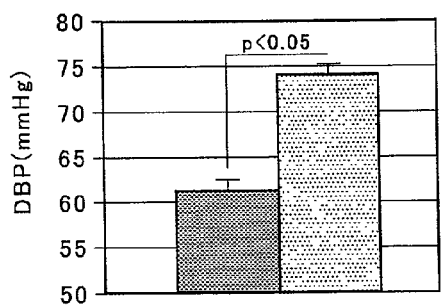

2) The diastolic blood pressure (DBP) was meaningfully higher (5%) (within physiologically normal range) after inhalation compared to before inhalation (FIG. 2B).

Figure 2E:
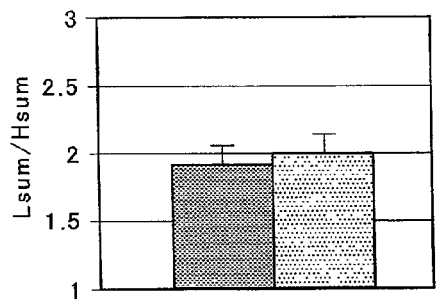
Figure 2C:
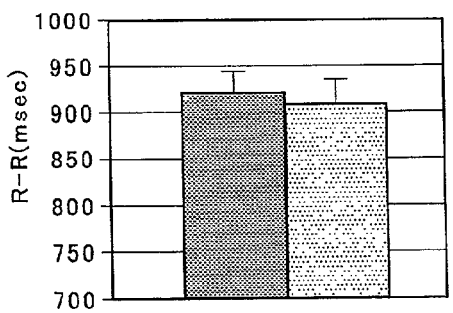

3) There was no meaningful change in ECG R—R interval after inhalation compared to before inhalation (FIG. 2C).

4) The Hsum tended to be lower (5%) inhalation compared to before inhalation (FIG. 2D).

5) The Lsum/Hsum tended to be higher after inhalation compared to before inhalation (FIG. 2E).

Figure 2F:
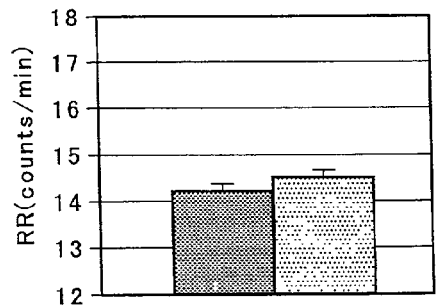

6) There was no meaningful difference in respiratory rate (RR) after inhalation compared to before inhalation (FIG. 2F).

Conclusion

The above results demonstrate that the inhalation of cedrol by the subjects resulted in a return to a state of equilibrium in various parts of the body, and suppressed parasympathetic overactivity while simultaneously elevating the sympathetic underactivity, thereby resulting in a suitable autonomic nervous balance.

Example 3

The subjects were ten women in their twenties suffering from poor sleep. ECG (chest V5 lead), brain waves (C3, O1 in the international 10–20 method), respiration (impedance method: abdomen and chest), superficial electromyogram (bipolar lead of left and right mentalis muscles), and ocular movement (bipolar lead without horizontally linking left and right eye-sockets) were monitored from the time the subjects went to bed until they woke in a 40 $m^2$ room. The cedrol was administered by placing Petri dishes filled with cedrol on 95° C. hot plates so that approximately 100 mg was vaporized per hour (about 1 ppb/hr), from the time subjects went to bed until they woke. Measurements were taken for 7 days. No administration took place on the first two days, in order to allow subjects to become acclimated to the measuring instruments and environment (control). On the third day, administration was managed without anything placed on the hot plates (placebo). After 3 days, cedrol was administered on the 7th day.

The subjects were interviewed about their condition on waking using a questionnaire based on POMS (profile of mood states) to assess mood. The changes in the parameters measured during the administration of cedrol and placebo treatment were compared.

Awakening and sleep stages were determined in accordance with international standards for determining sleep stages (Sleep Brain Wave Atlas, pp. 3–9, Ishiyaku Shuppan KK, published September, 1971, the relevant portions thereof which describe sleep analysis and standards are incorporated herein by reference). Frequency analysis of R—R interval fluctuations and statistical analysis of the measurement results were done in the same manner as in Example 1.

Results

Figure 3A:
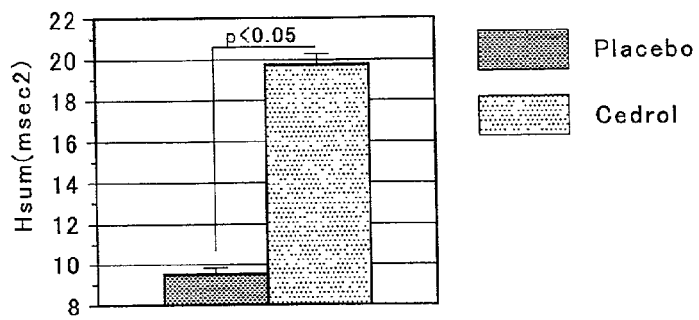
FIGS. 3A through 3D illustrate the measurement results for various test parameters of the autonomic nerve regulating agent (sleep improving agent) in Example 3.

1) Hsum was meaningfully increased (5%) during non-REM sleep when cedrol was administered compared to the placebo treatment (FIG. 3A).

Figure 3B:
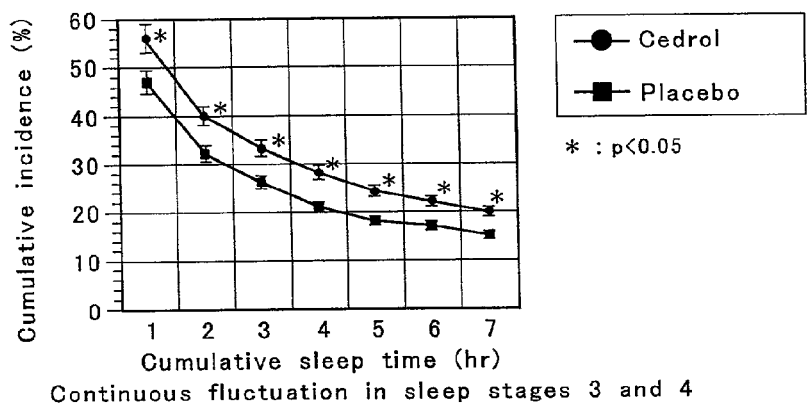

2) The cumulative incidence of stages 3 and 4 of sleep was meaningfully greater (5%) when cedrol was administered compared to the placebo treatment (FIG. 3B).

Figure 3C:
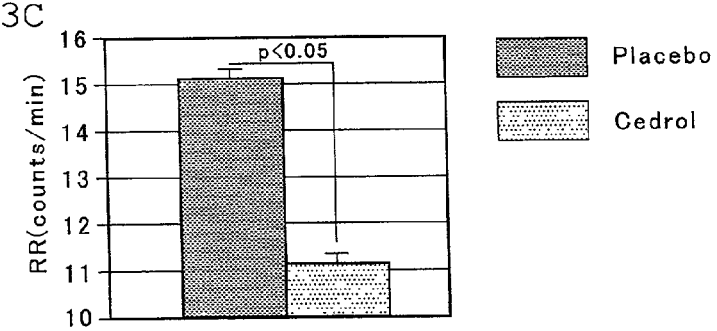

3) The respiratory rate (RR) was meaningfully lower (5%) during nor-REM sleep when cedrol was administered compared to the placebo treatment (FIG. 3C).

Figure 3D:
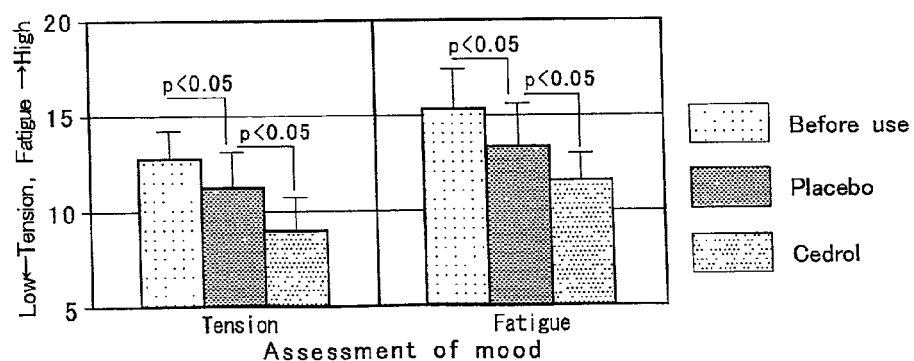

4) POMS revealed meaningful (5%) improvement in tension and fatigue when cedrol was administered on the 7th day compared to before administration and the 3rd day (placebo treatment) (FIG. 3D).

Conclusion

The above results reveal that subjects who slept while inhaling the fumes of cedrol (100 mg/hr) had a meaningfully deeper sleep, a longer non-REM sleep cycle, and a better quality of sleep, indicating a shift to parasympathetic predominance.

Example 4

Figure 4:
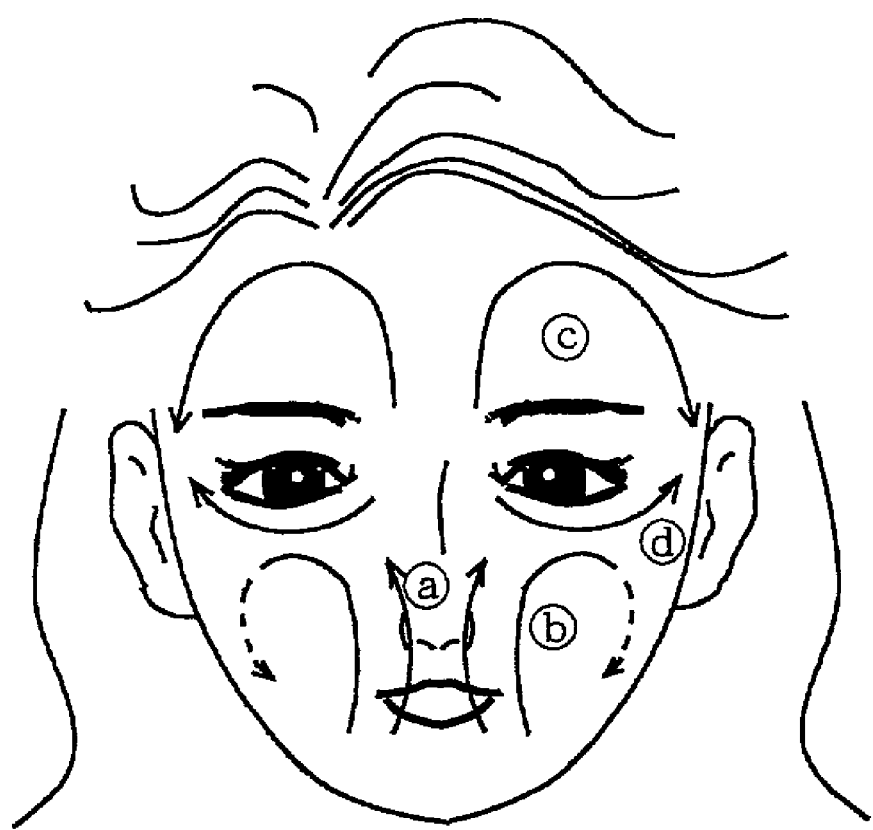
FIG. 4 illustrates a method for massaging the face.

The subjects were ten women in their twenties experiencing fatigue (sympathetic overactivity), who were asked to massage their faces as shown in FIG. 1 of Japanese Laid-Open Patent Application (Kokai) H10-113369 using the massage cream preparation in Table 1 once a day before sleep for 4 continuous weeks. Specifically, as shown in FIG. 4, (step 1) approximately 2 mL massage cream was spread on the hands and applied to the face, (step 2) the face was massaged 2 to 3 times with all four fingers (index to pinky) of both hands in a line from the corners of the mouth to the wings of the nose (direction (a) in FIG. 4), (step 3) the face was massaged 2 to 3 times in circles outward from the canter of the cheeks (direction (b) in FIG. 4), (step 4) the face was massaged 2 to 3 times in arcs outward from the center of the forehead (direction (c) FIG. 4), (step 5) steps 2 through 4 were repeated 3 times, and (step 6) the face under the eyes was massaged 3 times in arcs gradually extending outward (direction (d) in FIG. 4).

The ECG at rest (chest V5 lead), blood pressure (tonometry), and respiration (pulmonary volume instantaneously measured by respiratory rate sensor) were monitored in the morning before and 4 weeks after the beginning of massaging, so as to compare changes in the parameters. Frequency analysis of R—R interval fluctuations and statistical analysis of the measurement results were done in the same manner as in Example 1.

TABLE 1

| Components | Wt % |
|---|---|
| Oil components: | |
| beeswax | 6.0 |
| cetanol | 5.0 |
| reduced lanolin | 8.0 |
| squalane | 37.5 |
| fatty acid glycerin | 4.0 |
| Emulsifiers: | |
| oleophilic glycerin monostearate | 2.0 |
| polyoxyethylene (20 EO) sorbitan laurate ester | 2.0 |
| Aqueous phase: | |
| propylene glycol | 5.0 |
| purified water | 30.0 |
| cedrol | 0.5 |
| preservative/antioxidant | proper amount |

Results

Figure 5A:
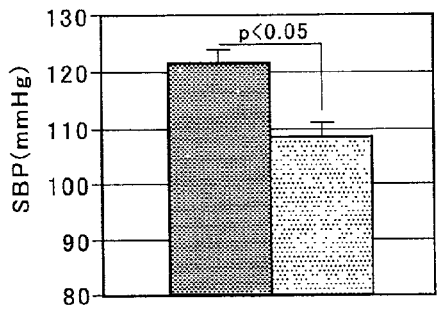
FIGS. 5A through 5F illustrate the measurement results for the various test parameters of the autonomic nerve regulating agent (massaging agent) in Example 4.

I) The systolic blood pressure (SBP) was meaningfully lower (5%) 4 weeks after the beginning of massaging compared to before massaging (FIG. 5A).

Figure 5D:
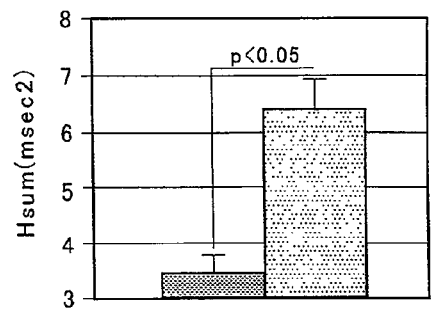
Figure 5B:
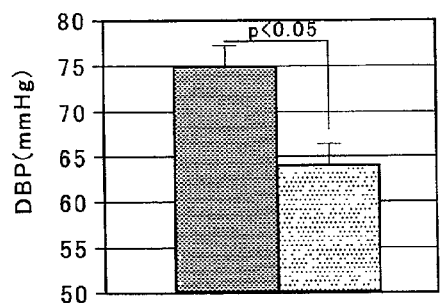

2) The diastolic blood pressure (DBP) was meaningfully lower (5%) 4 weeks after the beginning of massaging compared to before massaging (FIG. 5B).

Figure 5E:
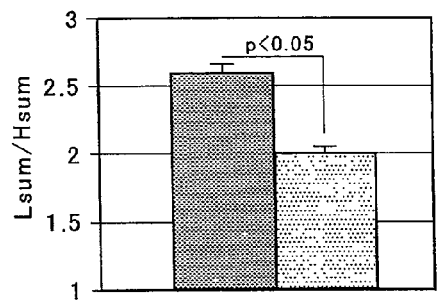
Figure 5C:
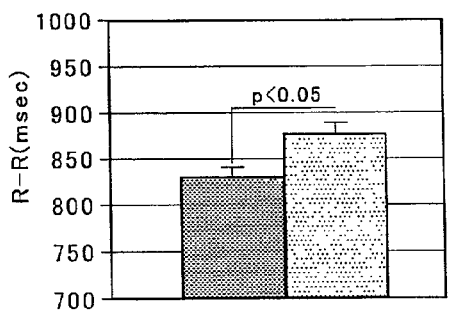

3) The ECG R—R interval was meaningfully longer (5%) 4 weeks after the beginning of massaging compared to before massaging (FIG. 5C).

4) The Hsum was meaningfully higher 4 weeks after the beginning of massaging compared to before massaging (FIG. 5D).

5) The Lsum/Hsum was meaningfully lower 4 weeks after the beginning of massaging compared to before massaging (FIG. 5E).

Figure 5F:
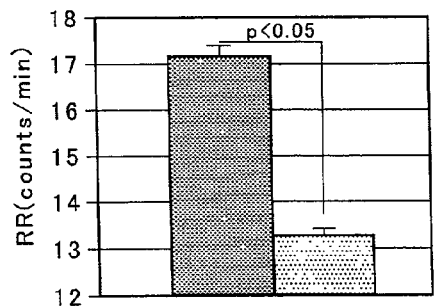

The respiratory rate (RR) was meaningfully lower (5%) 4 weeks after the beginning of massaging compared to before massaging (FIG. 5F).

Conclusion

The above results reveal that massaging the face using massage cream containing a cedrol blend once a day for 4 continuous weeks resulted in sedative effects in various parts of the body, the suppression of sympathetic overactivity, and a shift to parasympathetic predominance.

Example 5

The subjects were twenty women in their twenties experiencing mental and physical stress, who were asked to wear the following masks a) through d) (vaporization systems) around the mouth and nose at a temperature of 25° C. and a humidity of 50%;

(mask a)) mask incorporating a heating element (mask surface temperature about 70° C.) (mask described in Example 3 of Japanese Laid-Open Patent Application (Kokai) 2000-42125);

(mask b)) mask comprising a support (filter paper) impregnated on the surface with a prescribed amount of cedrol ($2.5 \times 10^{-3}$ g) and a mask incorporating a heating element (mask surface temperature about 70° C.) (mask described in Example 3 of Japanese Laid-Open Patent Application (Kokai) 2000-42125) the support being attached to the surface of the heating element;

(mask c)) mask incorporating a hot steam generating element (mask surface temperature about 70° C.; steam rate 0.5 g/min) (mask described in Example 1 of Japanese Laid-Open Patent Application (Kokai) 2000-42125); and (mask d)) mask comprising a support (filter paper) impregnated on the surface with a prescribed amount, of cedrol ($2.5 \times 10^{-3}$ g) and a mask incorporating a hot steam generating element (mask surface temperature about 70° C.; steam rate 0.5 g/min) (mask described in Example 1 of Japanese Laid-Open Patent Application (Kokai) 2000-42125), the support being attached to the surface of the hot steam generating element.

ECG (chest VS lead) and emotion spectrum analysis based on brain waves (T. Musha et al, ibid.) were performed for 3 minutes from 17 to 20 minutes after the masks had been applied. Frequency analysis of R—R interval fluctuations was performed for low frequency components integrating amplitudes 0.02 to 0.12 Hz (sum of low frequency: Lsum) and high frequency components integrating amplitudes 0.12 to 2.00 Hz (sum of high frequency: Hsum) using the rapid Fourier transform, as well as Lsum/Hsum.

The measurement results were statistically analyzed by multiple comparative analysis of variance.

Figure 6:
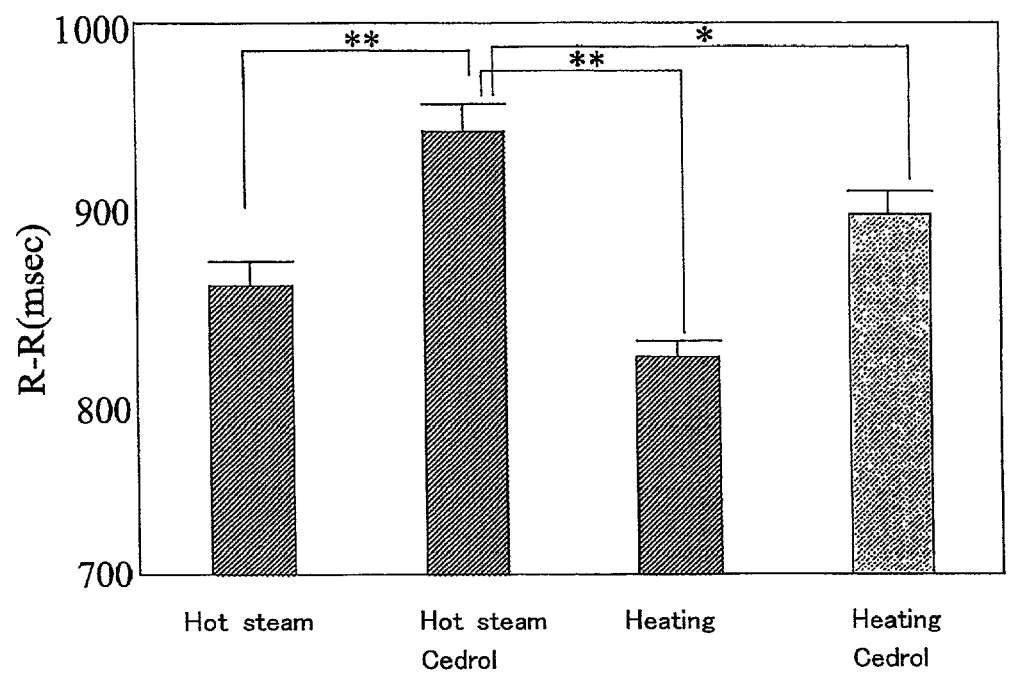
FIG. 6 illustrates the measurement results for R—R interval in ECG (electrocardiogram) when using the vaporization system (mask) in Example 5.

Results (1) The ECG R—R integral was meaningfully longer with the mask d) (hot steam+cedrol treatment) than with the other masks [mask d) $p<0.05$; other masks $p<0.01$] (FIG. 6).

Figure 7:
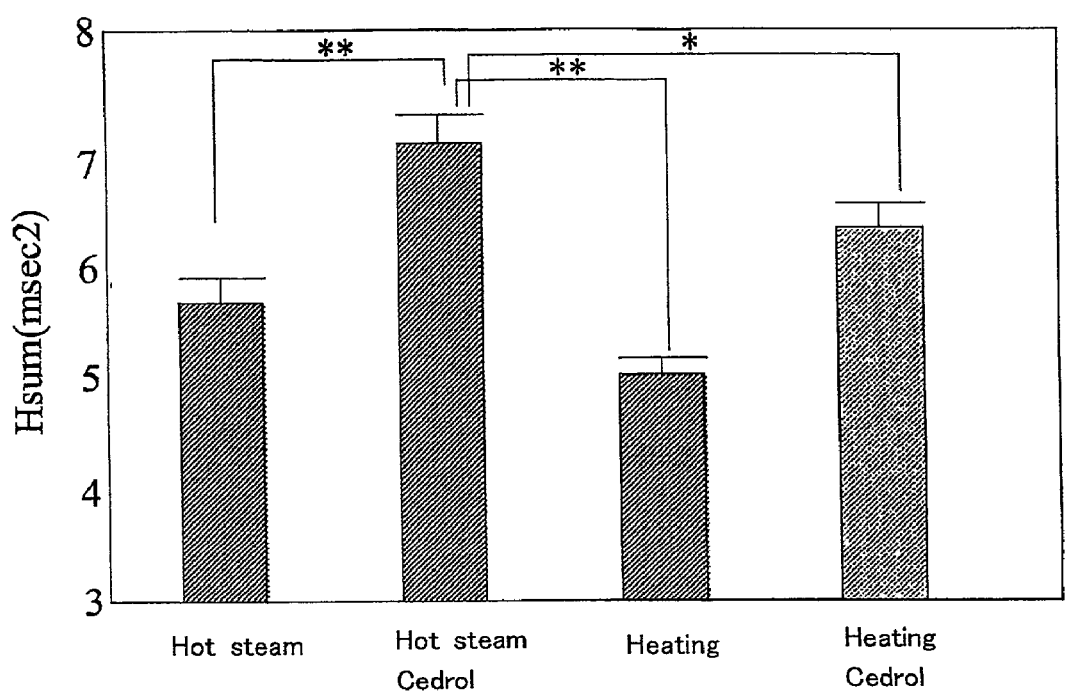
FIG. 7 illustrates the measurement results for Lsum/Hsum when using the vaporization system (mask) in Example 5.

(2) The Hsum was meaningfully greater with the mask d) (hot steam+cedrol treatment) than with the other masks [mask d) $p<0.05$; other masks $p<0.01$] (FIG. 7).

Figure 8:
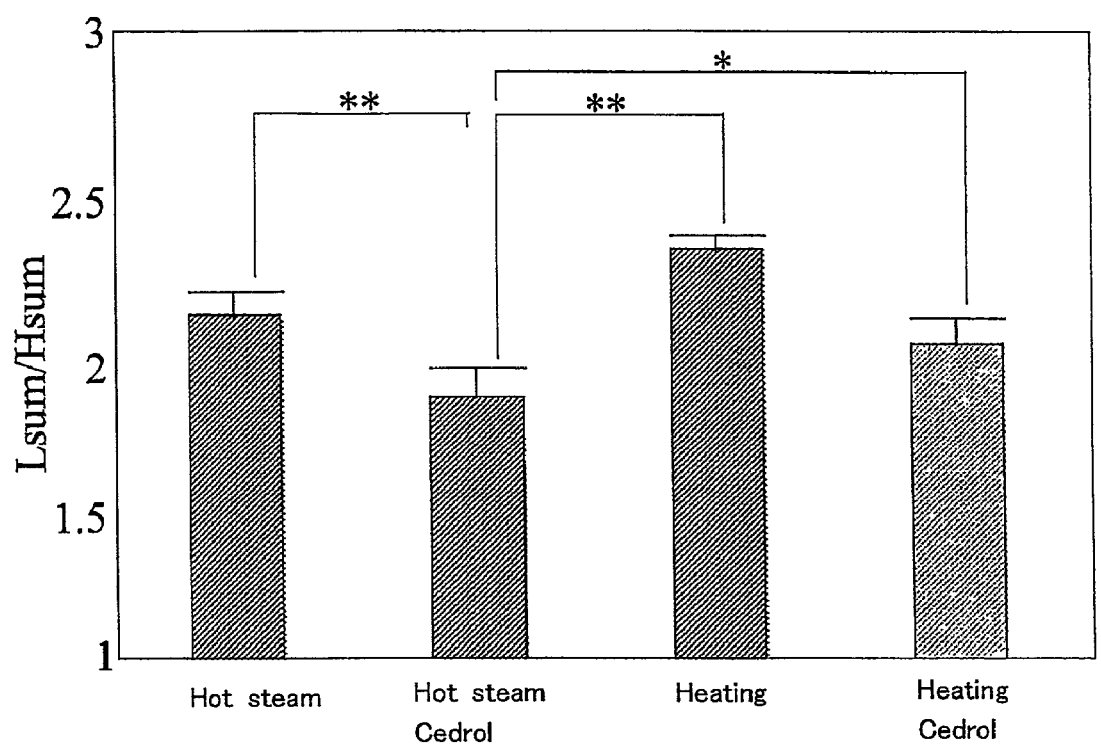
FIG. 8 illustrates the measurement results for Hsum when using the vaporization system (mask) in Example 5.

(3) The Lsum/Hsum was meaningfully lower with the mask d) (hot steam+cedrol treatment) than with the other masks [mask d) $p<0.05$; other masks $p<0.01$] (FIG. 8).

Figure 9A:
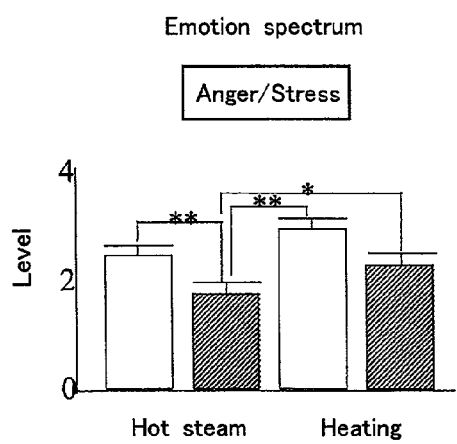
FIGS. 9A through 9D illustrate the results of emotion spectrum analysis when using the vaporization system (mask) in Example 5.
Figure 9B:
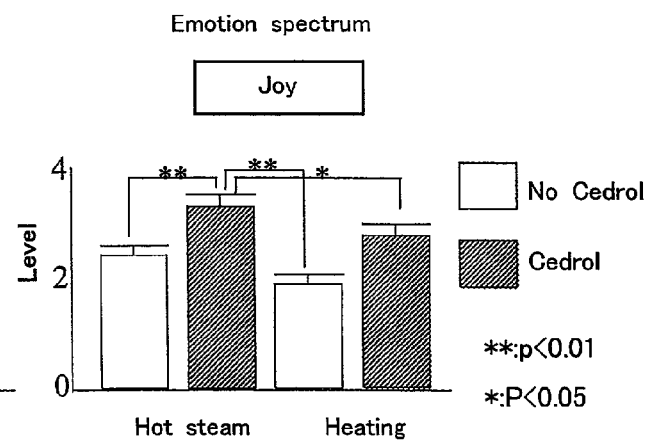
Figure 9C:
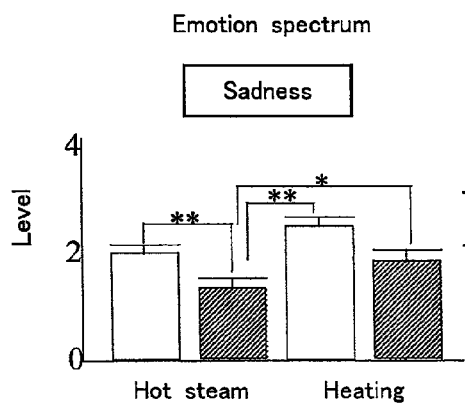
Figure 9D:
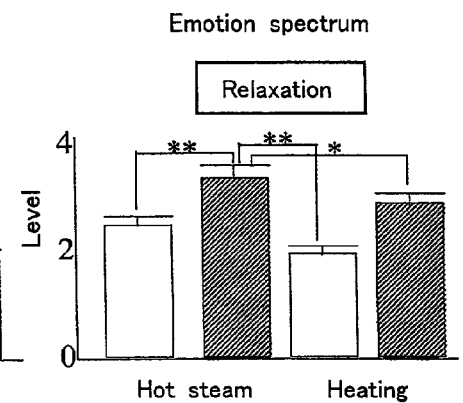

(4) the emotional spectrum was meaningfully improved in terms of anger/stress (FIG. 9A), joy (FIG. 9B), sadness (FIG. 9C), and relaxation (FIG. 9D) with the mask d) (hot steam+cedrol treatment.) than with the other masks [mask d) $p<0.05$: other masks $p<0.01$].

Conclusion

The above results demonstrate that the effects achieved through the inhalation of cedrol contained in the mask resulted in better calmness and tranquillity (relaxation effects) when used with hot steam than with heat. The effects appear to be peripheral effects in the various body parts as well as effects on the conscious level.

Example 6

The subjects were twenty women in their twenties experiencing mental and physical stress, who were asked to wear the following masks a) through d) (vaporization systems) around the mouth and nose at a temperature of 23° C. and a humidity of 50% while resting in a seated position for 30 minutes.

(mask a)) mask incorporating a heating element (mask surface temperature about 70° C.) (mask described in Example 3 of Japanese Laid-Open Patent Application (Kokai) 2000-42125):

(mask b)) mask comprising a support (filter paper) impregnated on the surface with a prescribed amount of cedrol ($2.5 \times 10^{-3}$ g) and a mask incorporating a heating element (mask surface temperature about 70° C.) (mask described in Example 3 of Japanese laid-Open Patent Application (Kokai) 2000-42125), the support being attached to the surface of the heating element;

(mask c)) mask incorporating a hot steam generating element (mask surface temperature about 70° C.; steam rate 0.5 g/min) (mask described in Example 1 of Japanese Laid-Open Patent Application (Kokai) 2000-42125); and (mask d)) mask comprising a support (filter paper) impregnated on the surface with a prescribed amount of cedral ($2.5 \times 10^{-3}$ g) and a mask incorporating a hot steam generating element (mask surface temperature about 70° C.; steam rate 0.5 g/min) (mask described in example 1 of Japanese Laid-Open Patent Application (Kokai) 2000-42125), the support being attached to the surface of the hot steam generating element. The masks were then removed, the subjects were asked to lie down, and the sleeping efficiency and intermittent awakening were assessed using actigrams while the subjects slept until the following day.

Statistical analysis of the measurement results was the same as in Example 5.

Figure 10:
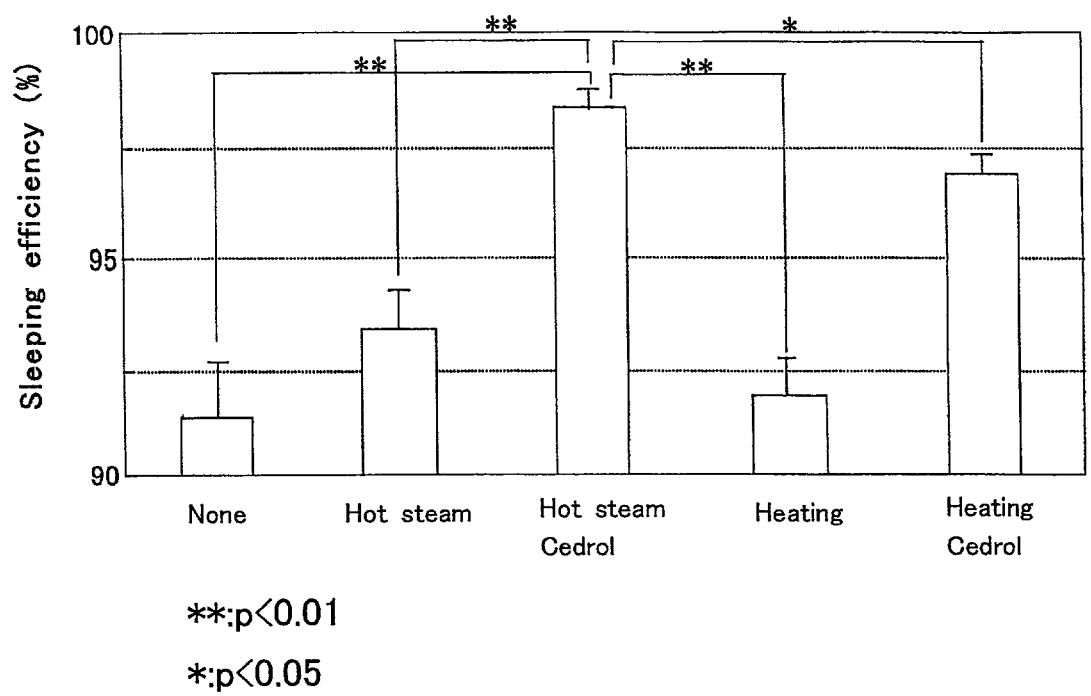
FIG. 10 illustrates the measurement results for sleeping efficiency when using the vaporization system (mask) in Example 6.

Results (1) Sleeping efficiency was meaningfully better with mask d) (hot steam+cedrol treatment) than with the other masks [mask d) $p<0.05$; other masks $p<0.01$] (FIG. 10).

Figure 11:
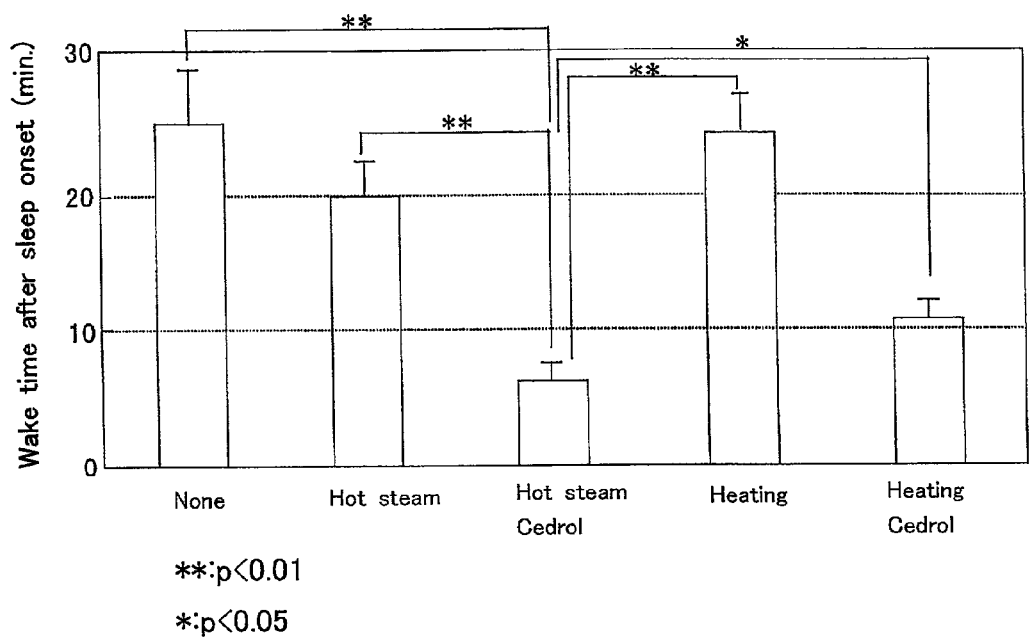
FIG. 11 illustrates the measurement results for intermittent awakening when using the vaporization system (mask) in Example 6.

(2) There were meaningfully fewer intermittent awakening with mask d) (hot steam+cedrol treatment) than with the other masks [mask d) $p<0.05$; other masks p 0.01] (FIG. 11).

Conclusion

The results demonstrate that the effects achieved through the inhalation of Cedrol contained in the mask resulted in better sleeping efficiency when used with hot steam than with heat.

Example 7

The subjects were twenty insomniac women in their fifties, while sleep was assessed from 3 hours before bed until wakening for 4 weeks in a room (sleeping room) at a temperature of 23° C. and a humidity of 50%. The first week served as a control. For the last 3 weeks, the test was conducted by replacing the curtains, wall paper, flooring, pillows, sheets, and bedding with those which had been coated with cedral (1.5 µg/cm$^2$).

The subjects ware actigrams for 4 continuous weeks on the opposite of their leading arm to allow assessment of the sleeping efficiency and intermittent awakening. Analyzed data for the cedrol coatings were from the 15th to 21st days following application.

Statistical analysis of the measurement results was the same as in Example 5.

Figure 12:
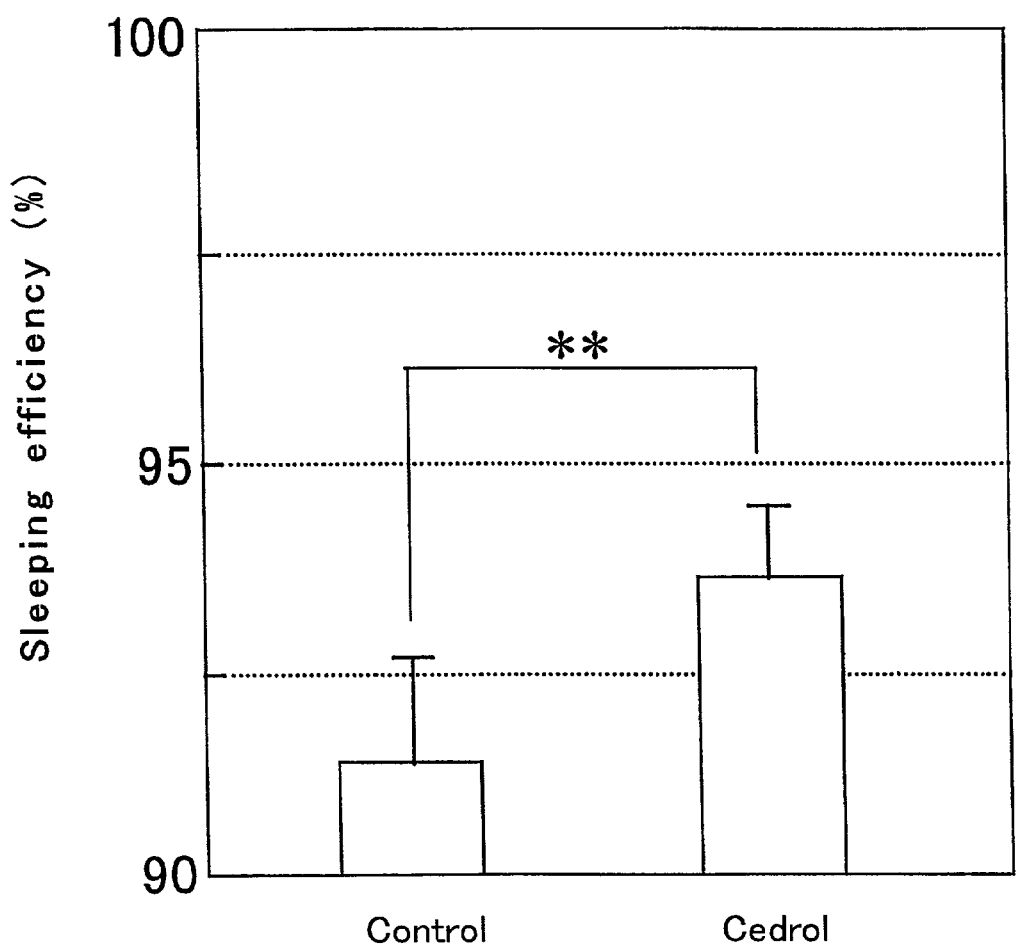
FIG. 12 illustrates the measurement results for sleeping efficiency when using the cedrol-treated bedding in Example 7.

Results (1) Sleeping efficiency was meaningfully better with cedrol treatment than during the control (p<0.01) (FIG. 12).

Figure 13:
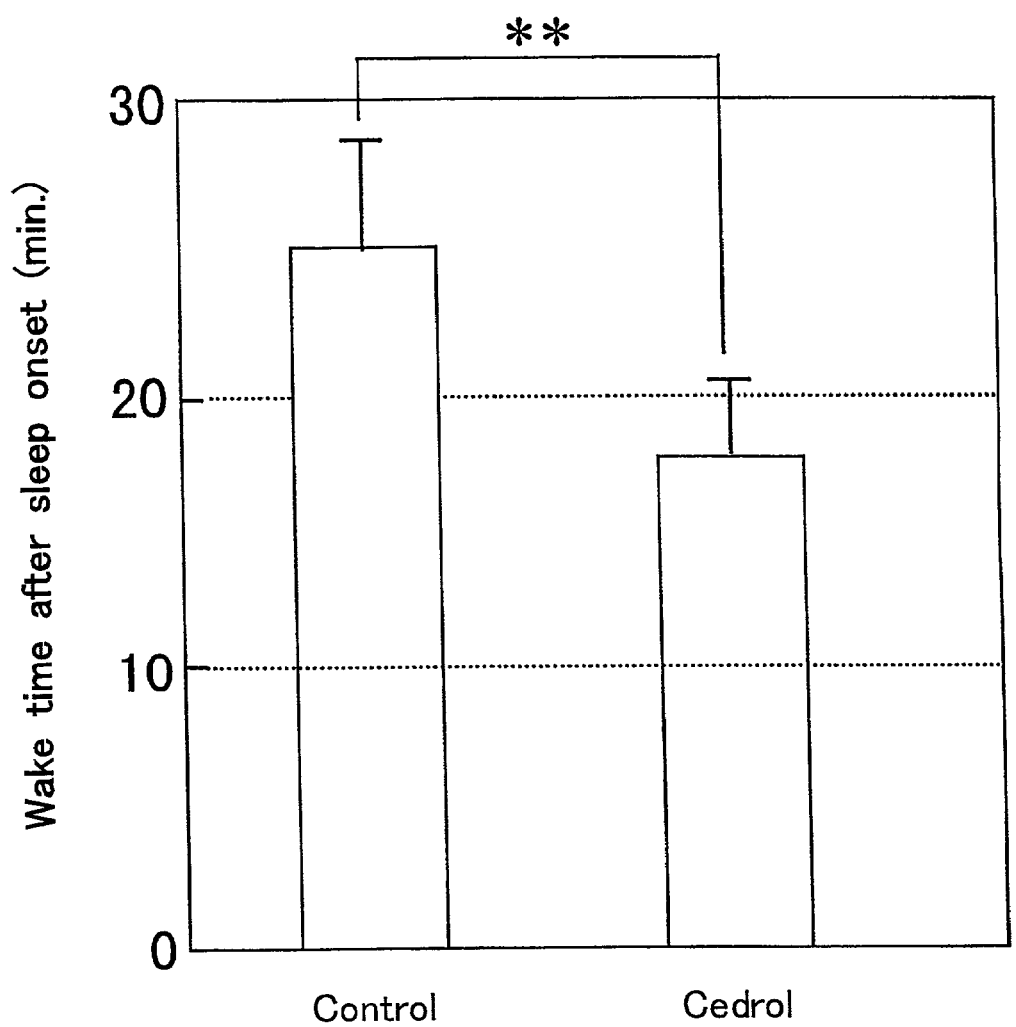
FIG. 13 illustrates the measurement results for intermittent awakening when using the cedrol-treated bedding in Example 7.

(2) There were meaningfully fewer intermittent awakening with cedrol treatment than during the control (p<0.01) (FIG. 13).

Conclusion

The results demonstrate that sleeping in a room using fiber products, furnishings, and bedding coated with cedrol resulted in far better sleep than when sleeping in a room using fiber products, furnishings, and bedding not coated with cedrol.

Example 8

The subjects were twenty women in their twenties experiencing mental and physical stress, who were acclimated for 20 minutes to a temperature of 25° C. and humidity of 50% as a control. ECG (chest V5 lead) and emotion spectrum analysis based on brain waves were conducted 20 minutes after the subjects licked one candy of 5 g containing no cedrol (58.0 wt % granulated sugar, 17.0 wt % water, 25 wt % starch syrup, and a suitable amount of coloring), or another candy of 5 g containing 0.01 wt % cedrol (58.0 wt % granulated sugar, 17.0 wt % water, 24.99 wt % starch syrup, 0.01 wt % cedrol, and a suitable amount of coloring), Frequency analysis of the R—R interval fluctuations and statistical analysis of the measurement results were the same as in Example 5.

Figure 14:
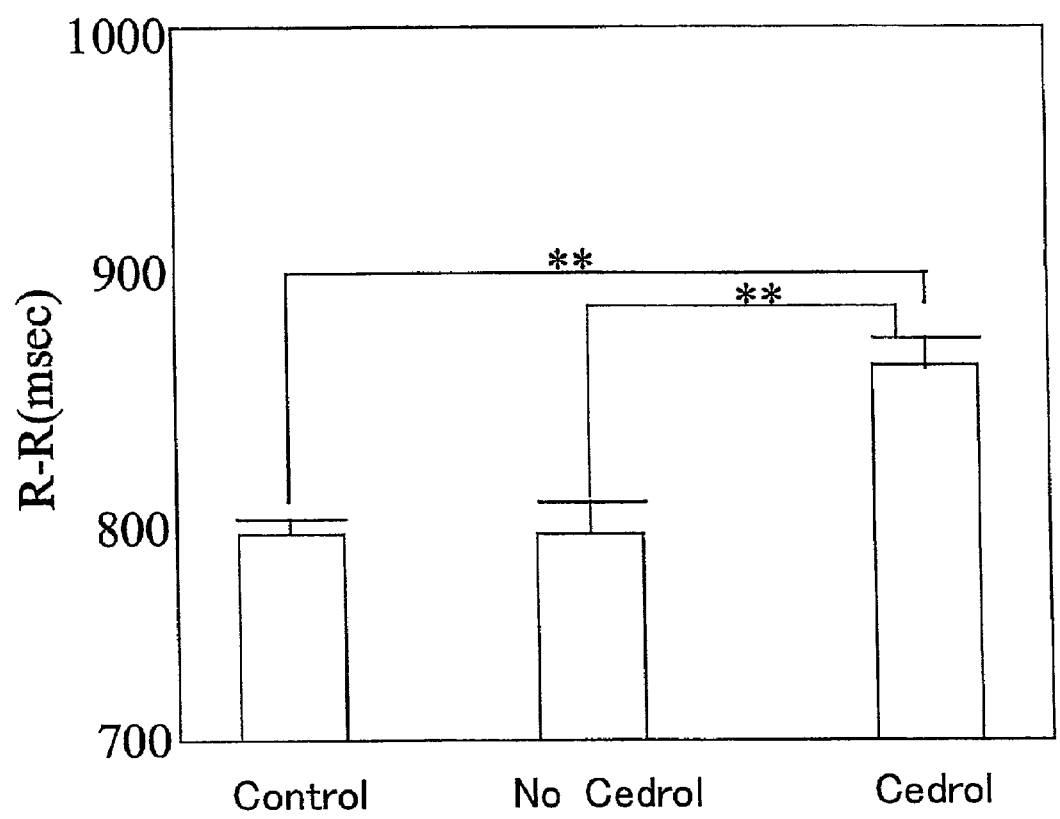
FIG. 14 illustrates the measurement results for R—R interval in ECG with the licking of candy containing cedrol in Example 8.
Figure 15:
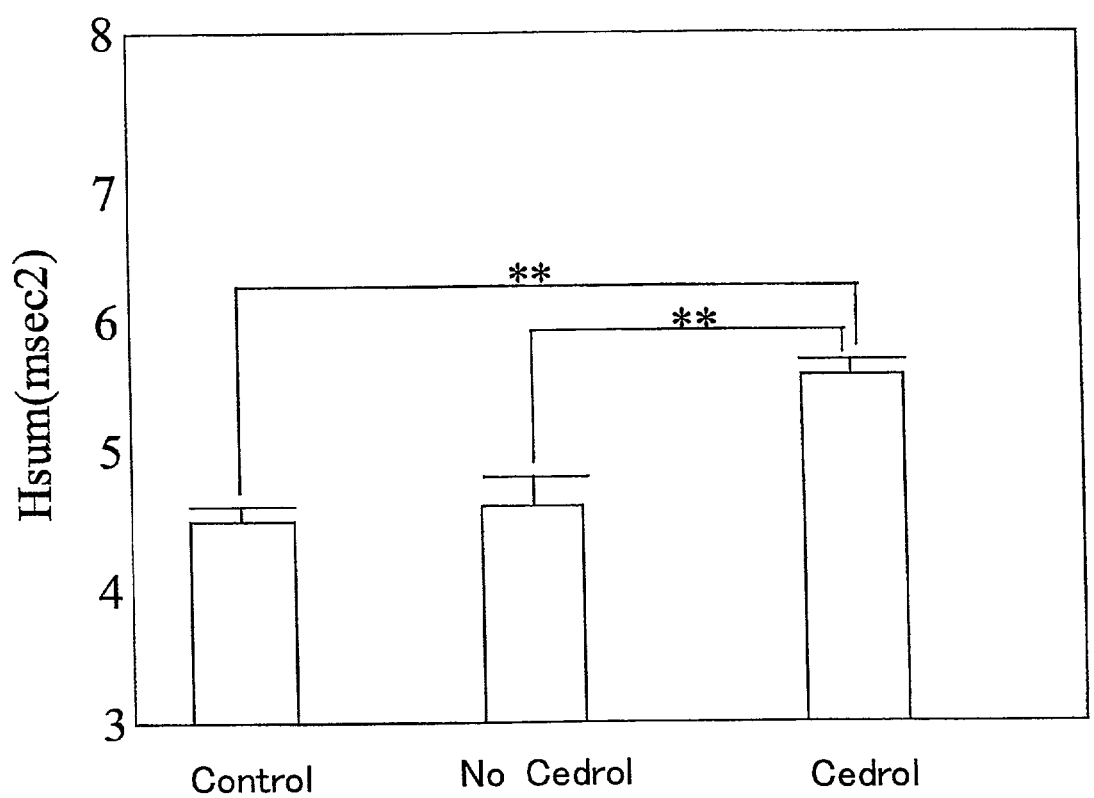
FIG. 15 illustrates the measurement results for Hsum with the licking of candy containing cedrol in Example 8.

Results (1) The ECG R—R interval was meaningfully longer (p<0.01) when the subjects licked the candy containing cedrol than during the control, and was also meaningfully longer (p<0.01) than when the candy containing no cedrol was licked (FIG. 14).

(2) The Hsum was meaningfully greater (p<0.01) when the subjects licked the candy containing cedrol than during the control, and was also meaningfully greater (p<0.01) than when the candy containing no cedrol was licked (FIG. 1b).

Figure 16:
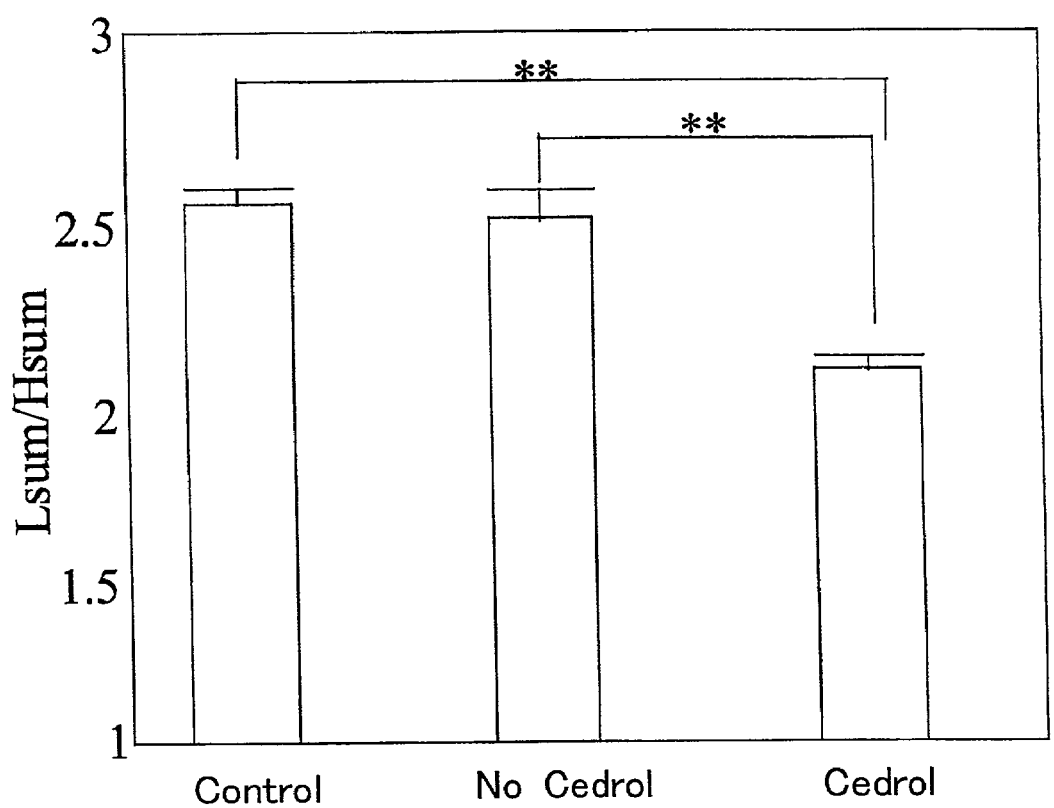
FIG. 16 illustrates the measurement results for Lsum/Hsum with the licking of candy containing cedrol in Example 8.

(3) The Lsum/Hsum was meaningfully lower (p<0.01) when the subjects licked the candy containing cedrol than during the control, and was also meaningfully lower (p<0.01) than when the candy containing no cedrol was licked (FIG. 16).

Figure 17A:
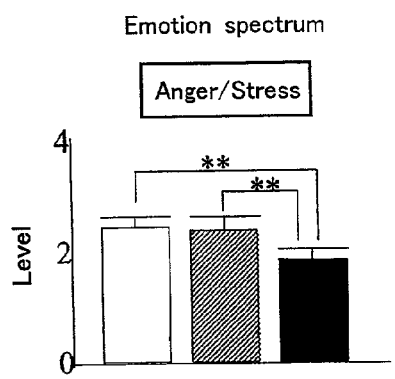
FIGS. 17A through 17D illustrate the results of emotion spectrum analysis with the licking of candy containing cedrol in Example 8.
Figure 17B:
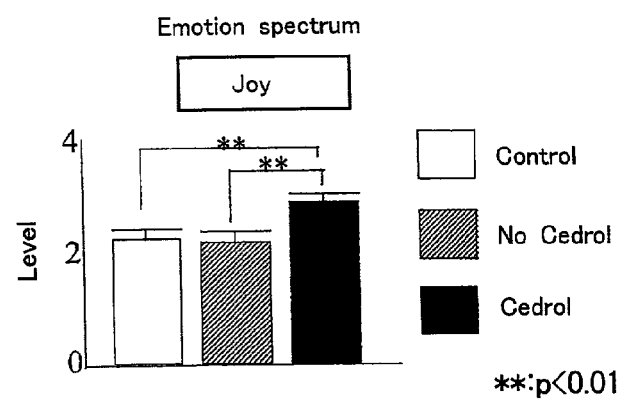
Figure 17C:
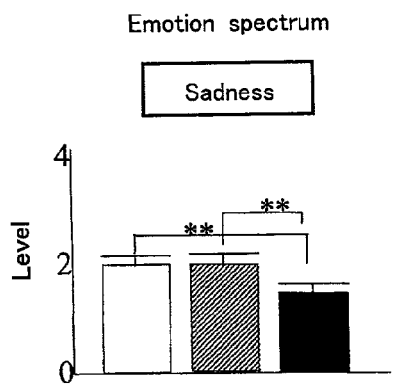
Figure 17D:
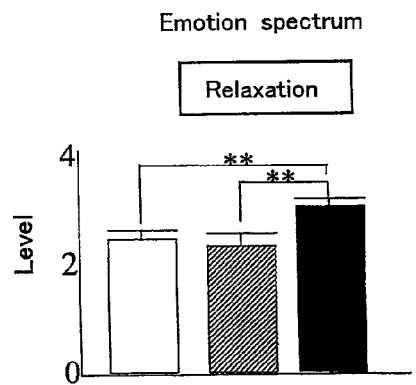

(4) The emotion spectrum was meaningfully improved (p<0.01) in terms anger/stress (FIG. 17A), joy (FIG. 17B), sadness (FIG. 17C), and relaxation (FIG. 17D) when the subjects licked the candy containing cedrol than during the control, and was also meaningfully improved (p<0.01) than when the candy containing no cedrol was licked.

Conclusion

The above results demonstrate that, the effects of the candy containing cedrol resulted in better calmness and tranquillity (relaxation effects) than the candy containing no cedrol.

The effects appear to be peripheral effects in the various body parts as well as effects on the conscious level.

INDUSTRIAL APPLICABILITY

The autonomic nerve regulating agents of the present invention comprise a sesquiterpene alcohol with a boiling point of 250° C. or higher (at atmospheric pressure), and act on individuals without any noticeable perception of odor. Typical action includes bringing about the relative predominance of the parasympathetic activity over the sympathetic activity in individuals with sympathetic overactivity (that is, sympathetic suppression and/or parasympathetic stimulation), as well as bringing about the relative predominance of the sympathetic activity over the parasympathetic activity in individuals with parasympathetic overactivity. The invention can thus control the balance between the parasympathetic and sympathetic activities, regardless of individual sensitivity to or preference for fragrances, can normalize autonomic nerve disequilibrium, and has favorable effects on individuals such as sedative, sleep improving, and stress mitigating effects.

The invention claimed is:

1. A method for regulating autonomic nerve activity by increasing an ECG R—R interval in a person in need thereof, comprising administering by inhalation a composition comprising a sesquiterpene alcohol selected from the group consisting of cedrol, cedrenol, globulol and a mixture thereof to said person in an amount effective for regulating autonomic nerve activity, wherein said composition has no odor above a detectable threshold.

2. The method claimed in claim 1, wherein said autonomic nerve regulated activity is at least one activity selected from the group consisting of sleep, stress, parasympathetic activity, sympathetic activity and mood.

3. The method claimed in claim 1, wherein the sesquiterpene alcohol is cedrol.

4. The method claimed in claim 3, wherein the cedrol is at least 97% pure.

5. The method claimed in claim 1, wherein the sesquiterpene alcohol is present in air at a concentration of from 0.01 to 100 ppb.

6. The method claimed in claim 1, wherein the composition is administered by spraying onto a bedding or a wall covering.

7. The method claimed in claim 1, wherein the composition is administered to a plurality of persons by dispersing said composition in a space.

8. The method claimed in claim 1, wherein the composition is administered by wearing a mask, wherein said mask comprises a heating element, a hot steam generating element and the sesquiterpene alcohol.

9. A method for regulating autonomic nerve activity by decreasing systolic blood pressure in a person in need thereof, comprising administering by inhalation a composition comprising a sesquiterpene alcohol selected from the group consisting of cedrol, cedrenol, globulol and a mixture thereof to said person in an amount effective for regulating autonomic nerve activity, wherein said composition has no odor above a detectable threshold.

10. The method claimed in claim 9, wherein said autonomic nerve regulated activity is at least one activity selected from the group consisting of sleep, stress, parasympathetic activity, sympathetic activity and mood.

11. The method claimed in claim 9, wherein the sesquiterpene alcohol is cedrol.

12. The method claimed in claim 11, wherein the cedrol is at least 97% pure.

13. The method claimed in claim 9, wherein the sesquiterpene alcohol is present in air at a concentration of from 0.01 to 100 ppb.

14. The method claimed in claim 9, wherein the composition is administered by spraying onto a bedding or a wall covering.

15. The method claimed in claim 9, wherein the composition is administered to a plurality of persons by dispersing said composition in a space.

16. The method claimed in claim 9, wherein the composition is administered by wearing a mask, wherein said mask comprises a heating element, a hot steam generating element and the composition comprising said sesquiterpene alcohol.

17. A method for regulating autonomic nerve activity by decreasing diastolic blood pressure in a person in need thereof, comprising administering by inhalation a composition comprising a sesquiterpene alcohol selected from the group consisting of cedrol, cedrenol, globulol and a mixture thereof to said person in an amount effective for regulating autonomic nerve activity, wherein said composition has no odor above a detectable threshold.

18. The method claimed in claim 17, wherein said autonomic nerve regulated activity is at least one activity selected from the group consisting of sleep, stress, parasympathetic activity, sympathetic activity and mood.

19. The method claimed in claim 17, wherein the sesquiterpene alcohol is cedrol.

20. The method claimed in claim 19, wherein the cedrol is at least 97% pure.

21. The method claimed in claim 17, wherein the sesquiterpene alcohol is present in air at a concentration of from 0.01 to 100 ppb.

22. The method claimed in claim 17, wherein the composition is administered by spraying onto a bedding or a wall covering.

23. The method claimed in claim 17, wherein the composition is administered to a plurality of persons by dispersing said composition in a space.

24. The method claimed in claim 17, wherein the composition is administered by wearing a mask, wherein said mask comprises a heating element, a hot steam generating element and the terpene alcohol.

* * * * *